United States Patent
Oldham

(10) Patent No.: US 6,865,423 B2
(45) Date of Patent: Mar. 8, 2005

(54) STIMULATION OF MUSCLES

(75) Inventor: Jacqueline A. Oldham, Manchester (GB)

(73) Assignee: The Victoria University of Manchester, Manchester (GB)

( * ) Notice: Subject to any disclaimer, the term of this patent is extended or adjusted under 35 U.S.C. 154(b) by 107 days.

(21) Appl. No.: 09/815,297

(22) Filed: Mar. 23, 2001

(65) Prior Publication Data

US 2002/0016617 A1 Feb. 7, 2002

Related U.S. Application Data

(63) Continuation-in-part of application No. 09/202,289, filed on Apr. 28, 1999, now Pat. No. 6,236,890, and a continuation of application No. PCT/GB97/01565, filed on Jun. 11, 1997.

(30) Foreign Application Priority Data

Jun. 13, 1996 (GB) .............................. 9612388
Oct. 25, 1996 (GB) .............................. 9622267
Nov. 23, 1996 (GB) .............................. 9624386

(51) Int. Cl.⁷ .............................. A61N 1/18
(52) U.S. Cl. ...................................... 607/48
(58) Field of Search ............................ 607/46, 48, 49, 607/66, 68, 70, 72, 74

(56) References Cited

U.S. PATENT DOCUMENTS

| | | |
|---|---|---|
| 4,177,819 A | 12/1979 | Kofsky et al. |
| 4,528,984 A | 7/1985 | Morawetz et al. |
| 4,535,777 A | 8/1985 | Castel |
| 4,712,558 A | 12/1987 | Kidd et al. |
| 4,719,922 A | 1/1988 | Padjen et al. |
| 5,018,524 A | 5/1991 | Gu et al. |
| 5,097,833 A * | 3/1992 | Campos .................. 607/68 |
| 5,285,781 A | 2/1994 | Brodard |
| 5,350,415 A * | 9/1994 | Cywinski .................. 607/68 |
| 5,433,737 A | 7/1995 | Aimone |
| 5,504,420 A | 4/1996 | Hamard et al. |
| 5,507,788 A | 4/1996 | Lieber |
| 5,562,718 A | 10/1996 | Palermo |
| 6,236,890 B1 * | 5/2001 | Oldham .................. 607/68 |

FOREIGN PATENT DOCUMENTS

| | | |
|---|---|---|
| FR | 0 197 889 | 3/1986 |
| GB | 1527908 | 10/1978 |
| GB | 2156682 | 10/1985 |
| GB | 2175806 | 9/1988 |
| WO | WO 87/00760 | 12/1987 |

OTHER PUBLICATIONS

"Rehabilitation of Atrophied Muscle in the Rheumatoid Arthritic Hand: A Comparison of Two Methods of Electrical Stimulation," *The Journal of Hand Surgery*, Oldham and Stanley, pp. 294–296, vol. 14–B. No. 3, Aug. 1989.

(List continued on next page.)

Primary Examiner—George R. Evanisko
(74) Attorney, Agent, or Firm—Nixon & Vanderhye, P.C.

(57) ABSTRACT

Electrical muscle stimulation relies upon the application to the muscles of a patient of a stimulating signal which comprises a series of regularly spaced bursts of pulses. Each burst includes a first component as a first continuous train of regularly spaced pulses and a second component as a series of regularly spaced second trains of regularly spaced pulses. The second component is combined with the first component and the spacing between successive pulses in the second pulse trains is less than the spacing between successive pulses in the first pulse train. A third component as a series of regularly spaced third trains of regularly spaced pulses may be combined with the first and second components, the spacing between successive pulses in the third pulse train being less than the spacing between successive pulses in the second pulse trains.

25 Claims, 13 Drawing Sheets

OTHER PUBLICATIONS

"Electrotherapeutic Rehabilitation of the Quadriceps in Elderly Osteoarthritic Patients: A Double Blind Assessment of Patterned Neuromuscular Stimulation," *Clinical Rehabilitation*, 1995; 9:10–20.

"The Use of Patterned Neuromuscular Stimulation to Improve Hand Function Following Surgery for Ulnar Neuropathy," *Journal of Hand Surgery*, T. Petterson et al, 1994, pp. 430–433.

* cited by examiner

US 6,865,423 B2

STIMULATION OF MUSCLES

RELATED APPLICATION

This is a continuation-in-part application to parent U.S. patent application Ser. No. 09/202,289, filed Apr. 28, 1999, now U.S. Pat. No. 6,236,890 (which is incorporated herein by reference in its entirety), and which in turn is a continuation under 35 U.S.C. § 120 (365) of then copending PCT/GB97/01565 filed Jun. 11, 1997.

BACKGROUND OF INVENTION

The present invention relates to a method for electrically stimulating a muscle in which a stimulating signal is applied to the muscle and an electrical muscle stimulator for applying such a stimulating signal to the muscle.

It is well known that muscle contraction is caused by neural stimulation. Contraction occurs when an action potential is conducted down a nerve to a neuromuscular junction, the signal is then communicated to muscle cells and leads to the stimulation of the release of calcium ions into the cytoplasm of muscle cells which thereby modifies interactions between contractile proteins resulting in muscular contraction.

It has been long established that the application of an electrical field to muscles results in an artificially induced contraction of said muscles. Furthermore, as well as directly causing muscular contraction, electrical stimulation at specific frequencies can also modify the phenotype of a muscle. For instance, prolonged stimulation of a fast-twitch muscle with a uniform frequency of 10 Hz results in the fast-twitch muscle developing slow-twitch characteristics, namely increased endurance, but with less power than would be normal for fast-twitch muscle. Conversely, prolonged stimulation of a slow-twitch muscle with an intermittent frequency of 30–50 Hz results in the slow-twitch muscle developing fast-twitch characteristics, namely increased power, but with less endurance than would be normal for slow-twitch muscle.

It has been suggested that electrical stimulation of muscles may be a useful means of improving strength and/or endurance of incapacitated muscle (due to injury, under-use or some pathological condition). For a number of years muscles have been stimulated by Faradic stimulation delivering uniform frequencies (of around 30–50 Hz) with the aim of beneficially affecting the muscle. However, these treatments have at best been ineffective and at the worst harmful to the muscle in the long term.

UK Patent GB 2 156 682 examined the electrical discharge of nerves innervating muscle with an aim of developing a means of beneficially stimulating muscle. It discloses a method of recording electrical discharges from nerves innervating muscles. A signal generated on the basis of the recording is then used to "electrotrophically" stimulate muscle. Electrotrophic stimulation is defined as "the electrical stimulation of muscle fibre using a stimulating signal containing information effective to cause structural and/or functional change of muscle fibre without requiring the muscle fibre to respond mechanically to the stimulation". However the stimulating signal of GB 2 156 682 is complex and difficult to generate.

Current neuromuscular products typically provide a stimulating pulsed waveform with wide variability. The shape of individual pulses may be for example symmetric biphasic pulses (for example a positive going square wave immediately followed by a negative going square wave of equal amplitude and width) or asymmetric biphasic (for example a positive going square wave immediately followed by a negative going exponentially decaying waveform. Typically clinicians are given control over a large number of parameters of the stimulation waveform, for example the pulse width (typical values are 100 ms to 300 ms), the ramp time during which the amplitude of the pulses is increased (typically 1 to 8 seconds), the frequency of the pulses (typically 2 to 150 Hz), the overall duration of a train of pulses used to contract a muscle (typically 1 to 30 seconds) and the duration of relaxation periods between successive pulse trains (typically 1 to 45 seconds). This level of variability is provided to allow clinicians to make their own choices of pulse patterns applied to the patient. Clinicians want this freedom because the effectiveness of one wavetrain pattern as compared to another is unknown and therefore clinicians tend to proceed on the basis of trial and error. Thus using the term "pulse" to signify a single electrical stimulation event in which an applied electrical voltage or current changes from a steady state baseline, each pulse generally consisting of both a single positive going phase and a single negative going phase, using the term "waveform" to represent the shape of an individual pulse, and using the term "wavetrain" to describe a series of pulses, the clinician can determine the amplitude and width of individual pulses, the waveform of individual pulses, the frequency of pulses within a single wavetrain and the duration of and spacing between successive wavetrains.

U.S. Pat. No. 5,097,833 (Campos) accurately describes known devices for maintaining or enhancing muscle tone by applying individual pulses each of which has positive and negative phases the waveforms of which are such that there is net zero charge. The waveform is not critical providing there is an equal positive and negative net charge in the positive going and negative going phases. Arranging waveforms to deliver net zero charge minimises but does not entirely remove patient discomfort. Campos states that it is known that the pulse frequency can be varied, the pulse width can be varied, and that the pulse rate and width can be preset to provide particular effects. Campos also acknowledges however that even with control of the pulse frequency or width discomfort can still arise and painful titanic contractions can be caused.

The approach suggested by Campos is to apply uniform frequency wavetrains for the whole treatment period, or to use successive wavetrains each for several minutes duration at least with successive wavetrains delivering pulses at different frequencies, the frequency within each wavetrain being uniform. Campos teaches that an evenly balanced (net zero charge) waveform may cause a "contractile imbalance" reducing the desired therapeutic effect, and notes that compensating for this by purely increasing the charge in one of the phases of the biphasic pulse will result in a charge which is not net zero and therefore will cause more discomfort. Campos seeks to overcome this problem by modifying the phasing of the pulses (i.e. by reversing the pulses such that some pulses have the positive going phase followed by the negative going phase whereas other pulses have the positive going phase following the negative going phase). Delays are also introduced between the positive and negative phases of individual pulses. According to Campos this counteracts the contractile imbalance problem whilst still maintaining a net zero charge, so as to give the optimum therapeutic effect that can be achieved with a particular wavetrain/waveform and the minimum discomfort.

Thus, Campos modifies an essentially continuous train of pulses by changing the phasing and delays between phases of individual pulses. Nevertheless Campos does use a large number of pulses which is likely to cause discomfort and requires a complex waveform generator which must be used to make complex adjustments to achieve what Campos assumes would be the optimum pattern of pulse phase reversals and delays.

SUMMARY OF INVENTION

It is an object of the present invention to provide an improved electrical muscle stimulator and an improved method for electrically stimulating a muscle.

According to the present invention, there is provided an electrical muscle stimulator comprising means for generating a predetermined stimulating signal and means for applying the signal to a muscle, wherein the signal comprises a series of regularly spaced bursts of pulses with each burst including a first component as a first continuous train of regularly spaced pulses and a second component as a series of regularly spaced second trains of regularly spaced pulses, the second component being combined with the first component and the spacing between successive pulses in the second pulse trains being less than the spacing between successive pulses in the first pulse train.

The invention also provides a method for electrically stimulating a muscle in which a stimulating signal is applied to the muscle, comprising:

a) generating the stimulating signal, the signal comprising a series of regularly spaced bursts of pulses with each burst including:
  (i) a first component as a first continuous train of regularly spaced pulses, and
  (ii) a second component as a series of regularly spaced pulses, wherein the second component is combined with the first component and the spacing between successive pulses in the second pulse trains is less than the spacing between the successive pulses in the first train, and b) applying the stimulating signal to the muscle.

Preferably, each burst of pulses includes a third component as a series of regularly spaced third trains of regularly spaced pulses, the third component being combined with the first and second components, and the spacing between successive pulses in the third pulse trains being less than the spacing between successive pulses in the second pulse trains. Each burst of pulses may consist of the same number of second and third pulse trains and preferably each third pulse train immediately precedes a respective second pulse train. Preferably each third train consists of two pulses.

Although ideally the three components and only the three components described above are incorporated in each burst of pulses, it may be that additional components may be incorporated into the pulse pattern. For example, a fourth component of higher frequency than the third component could be incorporated in each burst. Furthermore, although it is preferable for the third component of the relatively highest frequency to immediately precede a respective second pulse train, the third pulse train could be spaced from the second pulse trains. Additionally, there may be circumstances in which useful results can be achieved without the incorporation of the third pulse train component.

In one preferred embodiment of the invention, the first pulse trains consist of pulses at 500 millisecond intervals, each second pulse train consists of pulses at 20 millisecond intervals, and each third pulse train consists of pulses at intervals of 12 milliseconds or less, for example 8 milliseconds.

One of the advantages of the present invention as compared with the prior art is that a relatively small number of pulses is delivered in each burst of pulses. For example, a ten second burst may include only 80 pulses, in contrast to a ten second burst of conventional 50 Hertz form which would include 500 pulses. The reduced number of pulses results in less muscle fatigue and therefore improved physiological results.

The stimulator may be delivered to the user in the form of a battery powered hand-held unit with a single input/output connector, a battery charger, an electrode connector, and a computer connection cable, the battery charger, electrode connection and computer connection cable each being adapted to be connected to the single input/output connector such that the electrode connector cannot be connected to the hand-held unit if the hand-held unit is connected either to the battery charger or the computer connection cable. The hand-held unit may present buttons to a user to enable the user to adjust the amplitude of the pulses. The pulse width may be programmable via computer-generated signals applied to the single input/output connector. This would enable a clinician but not the user to adjust the pulse width. The hand-held unit could comprise means for storing patient treatment records data which could be output to for example a computer for processing and review by a clinician.

SUMMARY OF THE DRAWINGS

Embodiments of the present invention will now be described, by way of example, with reference to the accompanying drawings, in which.

DETAILED DESCRIPTION OF THE DRAWINGS

Figure 1:
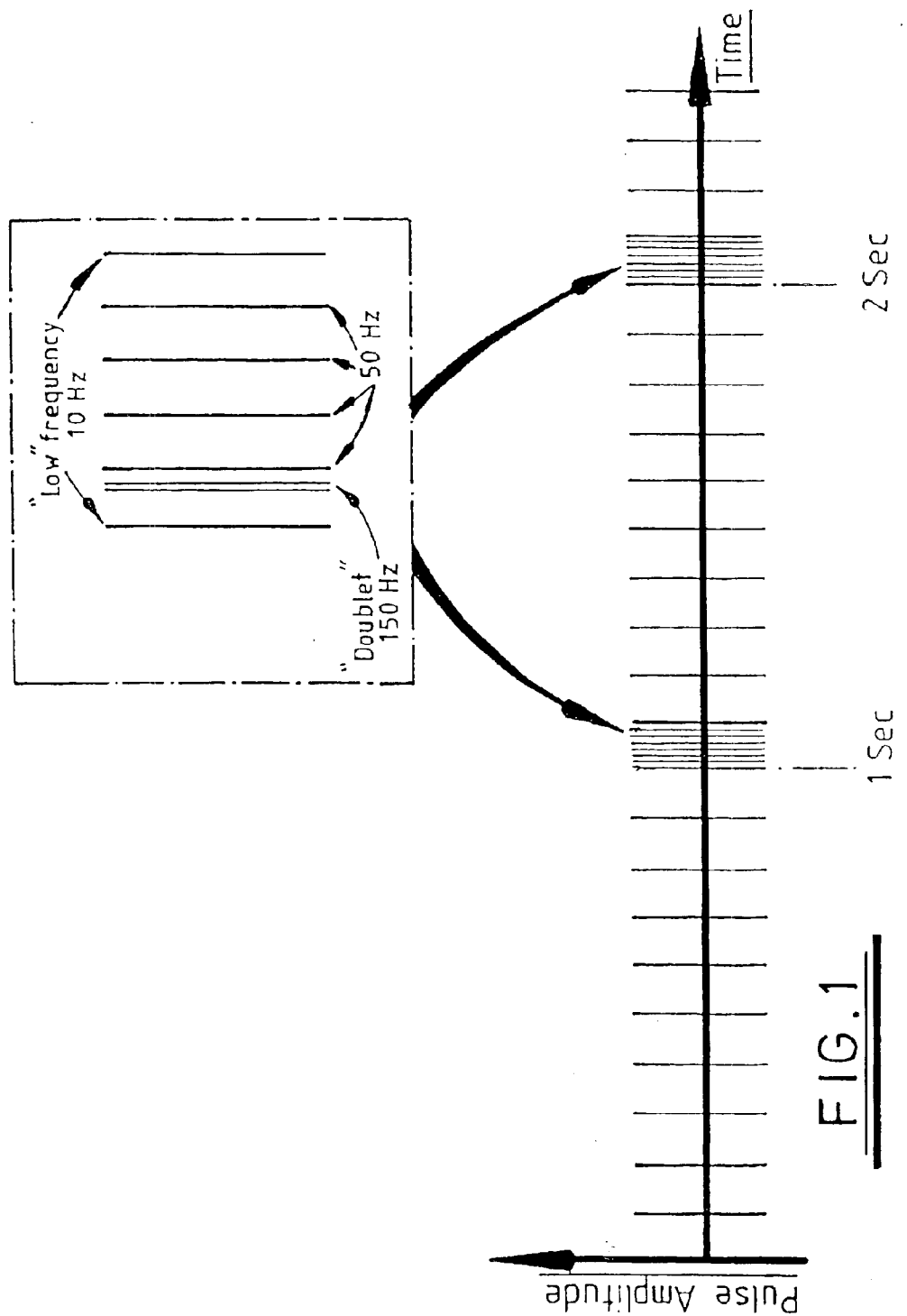
FIG. 1 illustrates one pulse pattern generated in an electrical muscle stimulator in accordance with a first embodiment of the invention.

FIG. 1 illustrates one pulse pattern generated in an electrical muscle stimulator in accordance with the invention. It will be noted that pulses are generated at regular intervals of 0.1 second such that the pulse pattern incorporates a continuous 10 Hz first component. At periodic intervals this continuous relatively low frequency component is combined with a second component in the form of a short pulse train of a higher frequency, in the illustrated case a series of four pulses at 0.02 second intervals such that the pulse repetition rate of the second component corresponds to 50 Hz. In addition, a third component in the form of a "doublet" of pulses is coupled with the second component, in the illustrated case the spacing between the two pulses of the doublet is 0.0066 seconds representing a pulse repetition rate of 150 Hz. It will be noted that in the case illustrated in FIG. 1 the third component immediately precedes the second component, although its position relative to the second component may differ from that shown in this example.

All of the pulses represented in FIG. 1 are of identical structure, each pulse including positive and negative-going components. Pulse shapes such as used in conventional muscle stimulation equipment may be used, the advantages of the invention arising from the pattern of such pulses rather than of the shape of individual pulses.

Good results have been achieved using the pattern of pulses represented in FIG. 1. It is believed however that a further improvement can be achieved by reducing the frequency of the low frequency component from 10 Hz as shown to 6 Hz or below.

It is believed that a course of treatment relying upon the described pulse pattern could be for one to three hours per day every day over a six to eight week period. The pulses could be applied to any muscle throughout the body via simple self-adhesive electrodes. The pulses are applied as a series of regularly spaced bursts with each burst including each of the three components. For example, pulse bursts can be delivered for "on" times of from ten to fifty seconds, with periods of inactivity, i.e. "off" times, of approximately the same duration. Good results have been obtained with "on" times of ten seconds in combination with "off" times of fifty seconds.

Figures 2, 3:
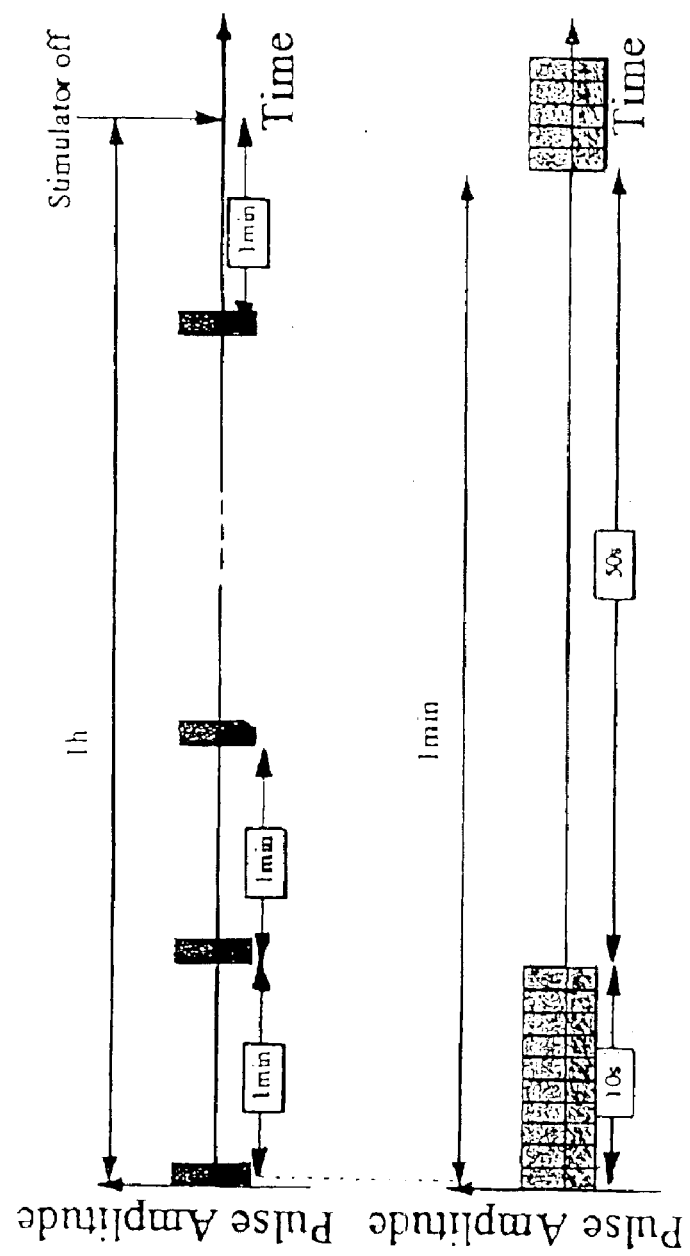
FIGS. 2 to 5 illustrate a pulse pattern generated in an electrical muscle stimulator in accordance with a second embodiment of the invention.

A second embodiment of the invention will now be described with reference to FIGS. 2 to 5. In the example illustrated in FIGS. 2 to 5, bursts of pulses are applied for "on" times of ten seconds separated by "off" times of fifty seconds. FIG. 2 represents a one hour duration course of treatment made up of sixty identical one minute sections, burst of pulses being applied during the course of the first ten seconds of each minute long section.

FIG. 3 represents the pulse amplitude in the first one minute section of FIG. 2. The first ten seconds of each one minute period is occupied by a burst of pulses made up from ten identical pulse patterns each having a duration of one second.

Figure 4:
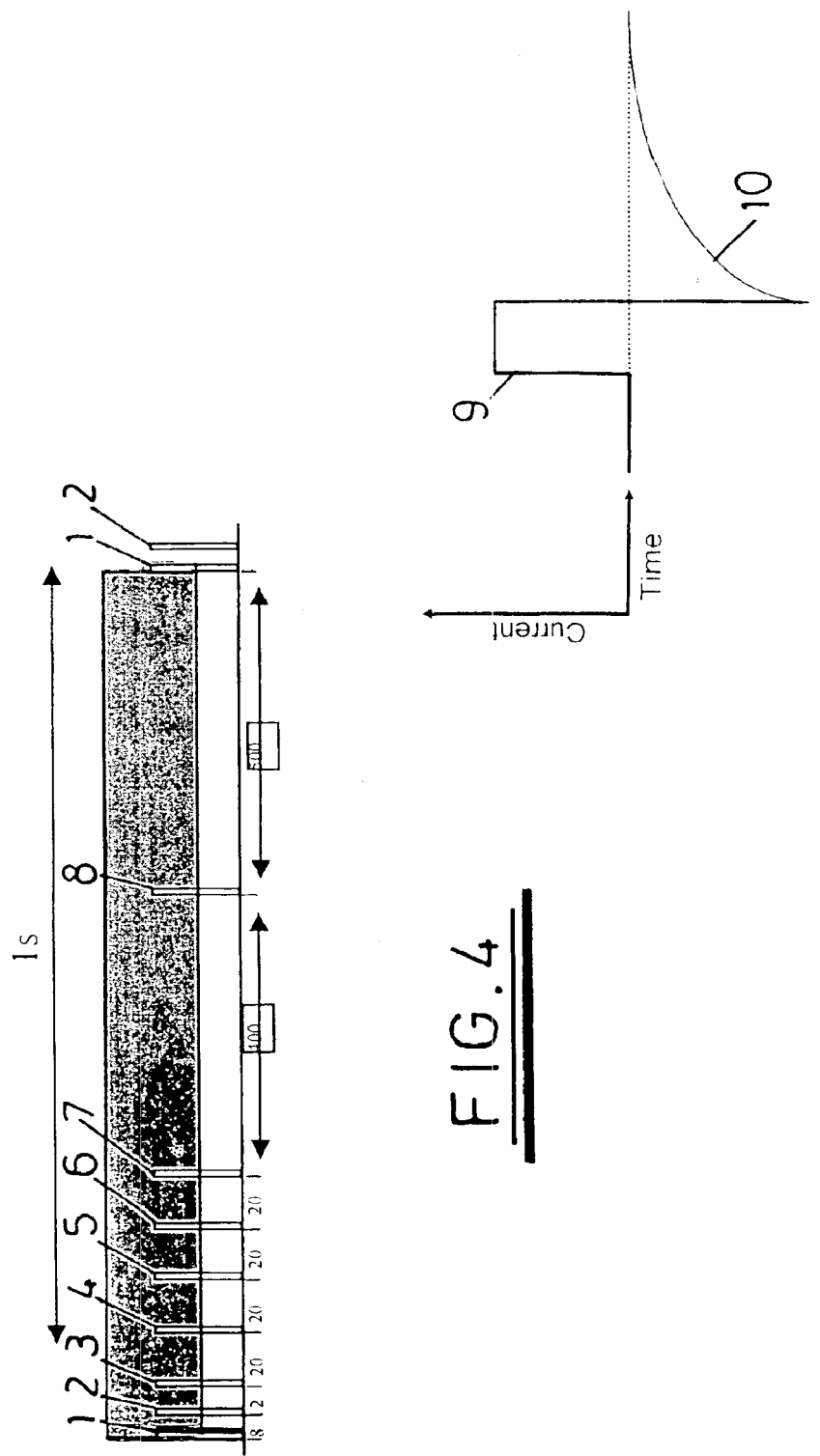

FIG. 4 represents the pulses applied in each of the ten seconds at the beginning of each one minute section showed in FIG. 2. There is a first pulse 1 triggered at the beginning of the one second period, a second pulse 2 triggered 8 milliseconds after the first pulse, a third, fourth, fifth, sixth and seventh pulses 3, 4, 5, 6 and 7 triggered respectively at 20, 40, 60, 80 and 100 milliseconds after the first, and an eighth pulse 8 triggered 500 milliseconds after the first pulse. Thus, in each ten second period as represented in FIG. 3, there is a first pulse train made up of twenty of the first and eighth pulses (1, 8) timed at 500 milliseconds intervals, ten second pulse trains with each of those second pulse trains being made up of the fourth, fifth, sixth and seventh pulses (4, 5, 6, 7), and ten third pulse trains with each of the third pulse trains being made up of the second and third pulses (2, 3) of each of the successive one second duration periods.

It will be appreciated that the three components of the pulse pattern of ten seconds duration illustrated in FIGS. 2 to 4 could be described in a different way, that is as a first pulse train made up of ten pulses at 1000 milliseconds intervals (pulses 8), ten second pulse trains with each of those second pulse trains being made up of the third, fourth, fifth, sixth and seventh pulses (3, 4, 5, 6, 7), and ten third pulse trains, with each third pulse train being made up of the first and second pulses (1, 2). A still further way of describing the pulse pattern would be on the basis that pulse 1 belongs to all three component pulse trains, that is the first pulse of a train of twenty pulses at 500 milliseconds spacings, the first pulse of a train of six pulses at twenty milliseconds spacings, and the first pulse of a train of two pulses at 8 milliseconds spacing. Whichever description of the pulse pattern is followed, however, it is clear that there are three components in each ten second burst, that is a first continuous component of relatively low frequency, a second intermittent component of relatively higher frequency, and a third intermittent component of still higher relative frequency.

As an alternative to the pulse pattern shown in FIG. 4, in which pulses are timed as 0, 8, 20, 40, 60, 80, 100 and 500 milliseconds repeated each second, pulses could be generated at 0, 8, 28, 48, 68, 88, 108 and 500 milliseconds repeated each second. Such a pattern could be described as including only two components, that is a first component made up of two pulses per second at 500 milliseconds intervals, and a second component made up of six pulses per second at 20 millisecond intervals starting with a first pulse at 8 milliseconds. That same pattern could also be described as including three components, that is a first component made up of two pulses per second at 500 millisecond intervals, a second component made up of five pulses at 20 millisecond intervals starting with a first pulse at 28 milliseconds, and a third component of 8 millisecond intervals made up of the pulses at 0 and 8 milliseconds, the pulse at 0 milliseconds contributing to both the first and third components.

Figure 5:
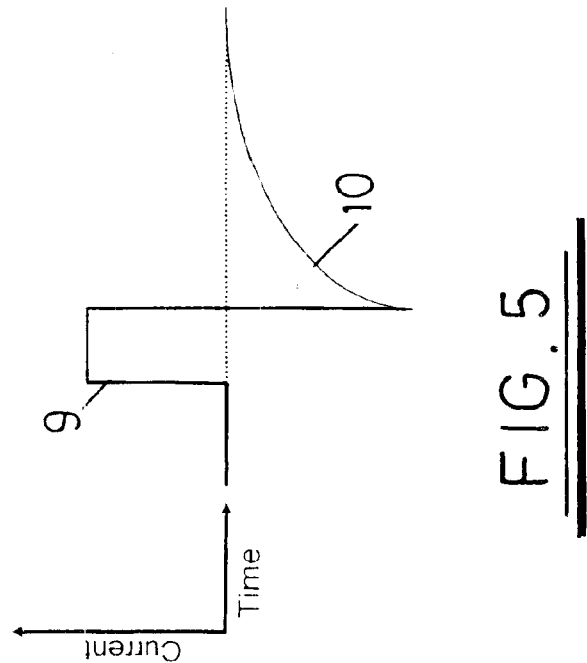

Referring to FIG. 5, this illustrates the waveform of each of the pulses represented in FIGS. 2 to 4. It will be seen that each pulse comprises a positive going square wave current pulse 9 followed by a negative going exponentially decaying pulse 10. As described in greater detail below, the amplitude of the positive going portion 9 of the waveform can be varied by the patient, for example between zero and 90 mA, the width of the pulse portion 9 can be varied by the clinician, for example between 50 ms and 350 ms, and the system is set up such that the area of the negative pulse portion 10 is substantially equal to the area of the positive pulse portion 9 with each of the areas being limited to a maximum of for example 50 $\mu$C.

It will be appreciated to that in FIGS. 2, 3 and 4 only positive going portions of each pulse are represented so to make it easier to illustrate the position of the pulses relative to the time axis. Each such pulse would however have the form represented in FIG. 5, that is a square-wave positive going portion 9 and a negative going portion 10.

An embodiment of a muscle stimulator designed to deliver the pattern of pulses described with reference to FIGS. 2 to 5 will now be described with reference to FIGS. 6 to 14.

Figure 6:
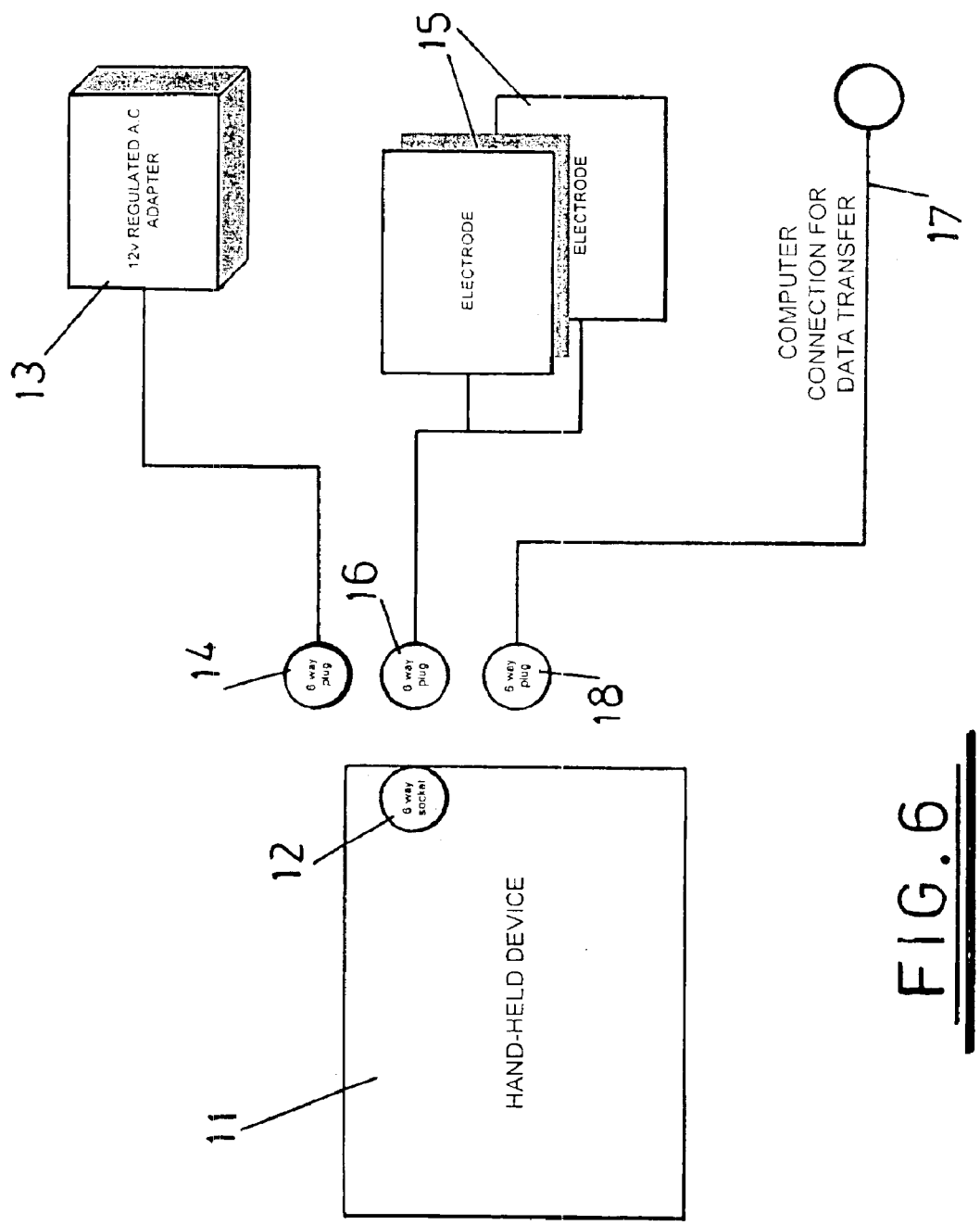
FIG. 6 represents physical components of a hand-held muscle stimulator in accordance with the present invention as delivered to a user.

FIG. 6 represents the physical components delivered to users, that is a handheld device 11 having a six way input socket 12, a 12 volt regulated AC adapter 13 having a six way plug 14 adapted to fit in the socket 12, two electrodes 15 each coupled to a single six way plug 16 adapted to be inserted into the socket 12, and a connection cable 17 coupled to a six way plug 18 also adapted for insertion into the socket 12.

In use, the electrodes 15 are applied to a patient's body as appropriate and the plug 16 is inserted into the socket 12. The handheld device 11 incorporates a rechargeable battery which can be recharged as necessary by inserted the plug 14 into the socket 12. Thus only one of the plugs 14 and 16 can communicate with a handheld device 11 at any one time and therefore there can be no risk to a patient to whom the electrodes 15 have been applied. Similarly, if information is to be downloaded from the handheld device 11 or the functioning of the handheld device 11 is to be adjusted the plug 18 is inserted into the socket 12 so as to enable communication between the handheld device 11 and a computer connected to the cable 17. Thus, as only one of the plugs 14, 16 and 18 can communicate with the device 11 at any one time, there can be no risk to a user as the electrodes 15 must be isolated from the handheld device 11 if the handheld device is connected either to the charger or a computer.

Figure 7:
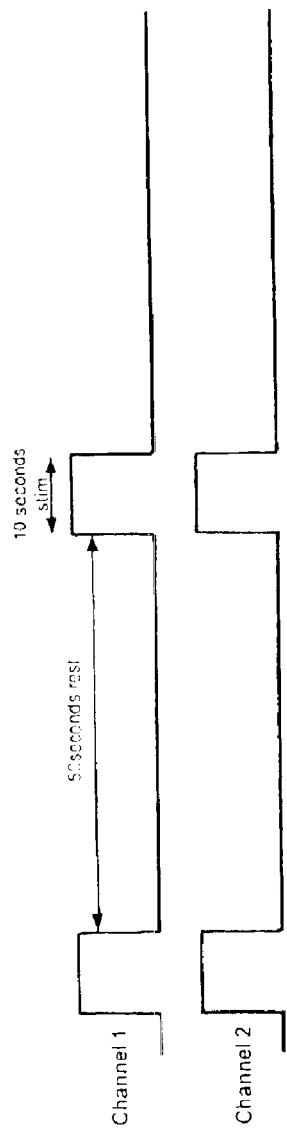
FIG. 7 represents signals applied to two channels of the stimulator of FIG. 6.
Figure 8:
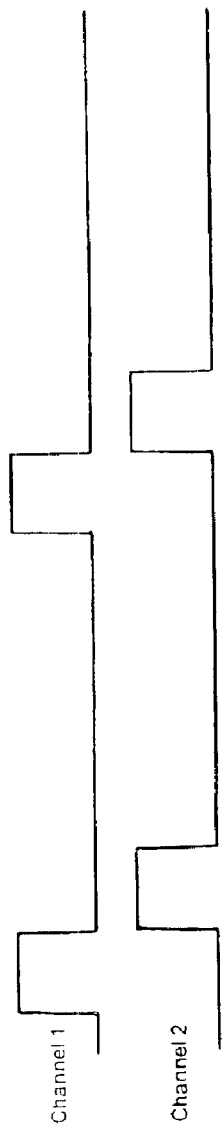
FIG. 8 illustrates an alternative signal pattern to that shown in FIG. 7.

Given that there are two electrodes 15, the device has in effect two channels, each channel being coupled to one of the electrodes. Identical in-phase signals may be applied to the two channels as represented in FIG. 7 to achieve co-contraction, or identical but out of phase signals may be applied to the two channels as represented in FIG. 8 to achieve reciprocal contractions.

Figure 9:
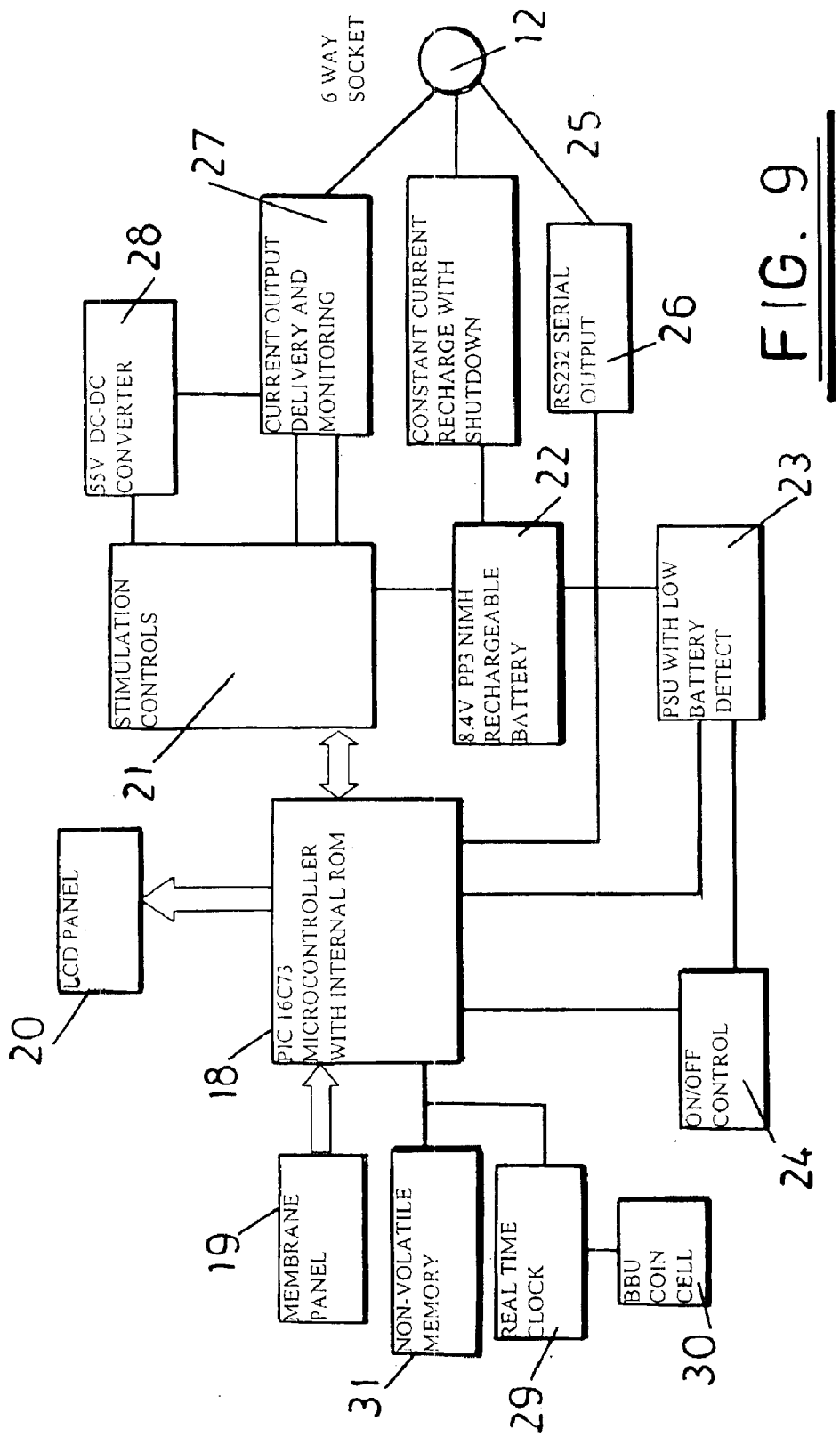
FIG. 9 schematically represents components incorporated in the hand-held device shown in FIG. 6.

FIG. 9 illustrates components incorporated in the handheld device 11 of FIG. 6. The heart of the system is a micro controller 18 to which the user can input control signals via a keyboard located behind a waterproof membrane panel 19 and which in turn outputs display data to an LCD panel 20 and control signals to a stimulation control unit 21. Power is derived from a rechargeable battery 22 coupled to the micro controller through a low battery detector circuit 23 and an on/off control switch 24. The battery is rechargeable from the six-way socket 12 of a constant current recharge circuit 25. Data can be input to an output from the micro controller 18 via an RS232 serial output circuit 26 coupled to the six-way socket 12. Stimulation current is delivered via an output circuit 27 coupled to a DC-DC converter 28 capable of boosting the battery voltage up to 55 volts DC.

The system also incorporates a real time clock 29 powered by a separate battery 30 so as to maintain clock operation even if the rechargeable battery 22 becomes fully discharged. A non-volatile memory 31 ensures that system functionality is maintained even if the rechargeable battery 22 becomes fully discharged.

Figure 10:
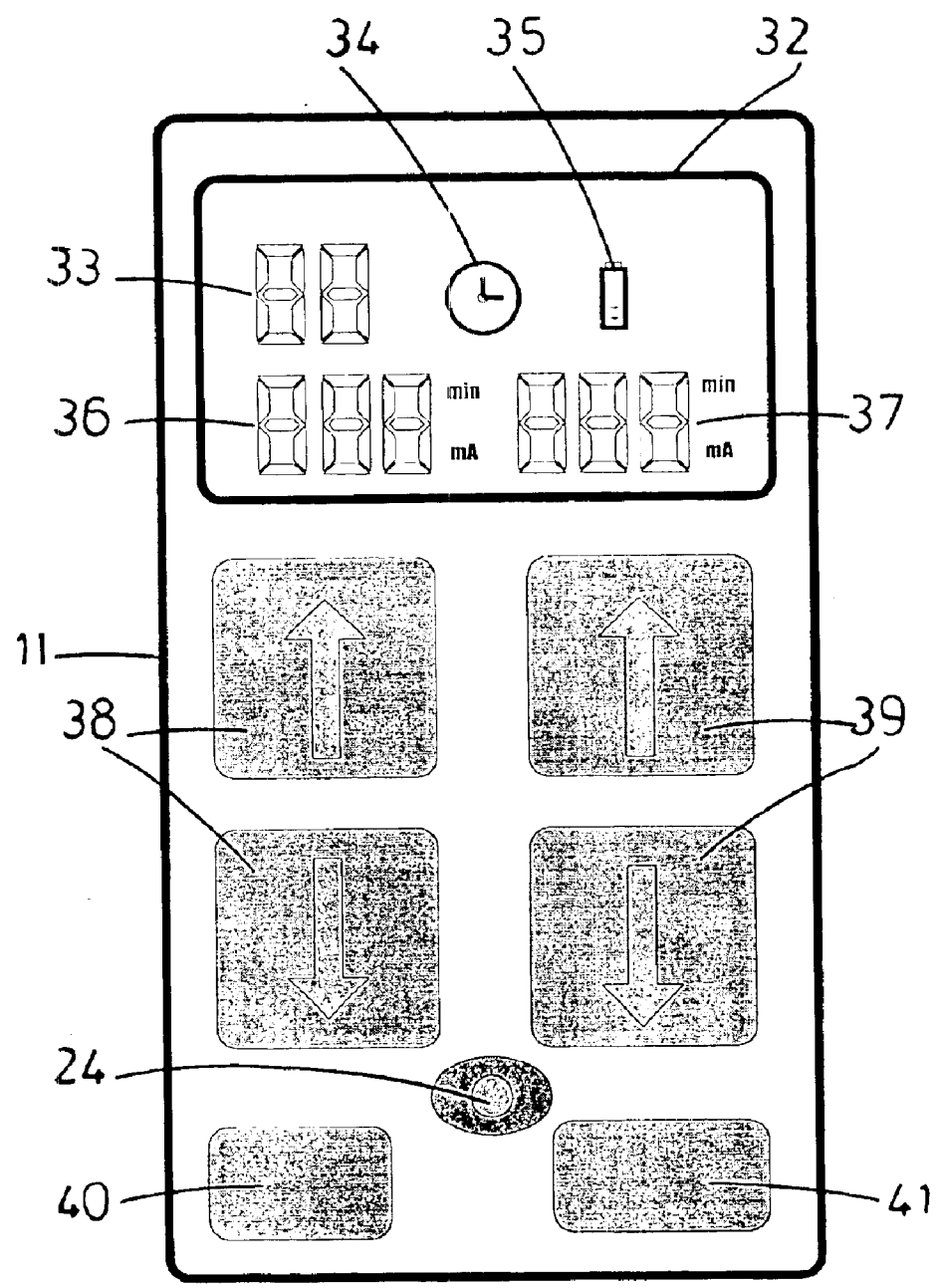
FIG. 10 illustrates the overall appearance of the hand-held device of FIG. 6.

FIG. 10 illustrates the appearance of the handheld device 11 of FIG. 6. A liquid crystal display 32 has a two digit display area 33 which indicates the treatment time left, a clock symbol 34 which is illuminated when stimulation is occurring and flashes during inter-stimulation rest periods, and an indicator 35 which illuminates when the rechargeable battery is approaching full discharge. A three digit display area 36 displays data relevant to channel 1 and a three digit display area 37 displays data relevant to channel 2. Buttons 38 can be depressed to control channel 1 and buttons 39 can be depressed to control channel 2. The on/off button 24 of FIG. 9 corresponds to the button 24 of FIG. 10. A button 40 can be pressed by the patient to set up a treatment session and a button 41 can be pressed to pause or restart a treatment session.

Figure 11:
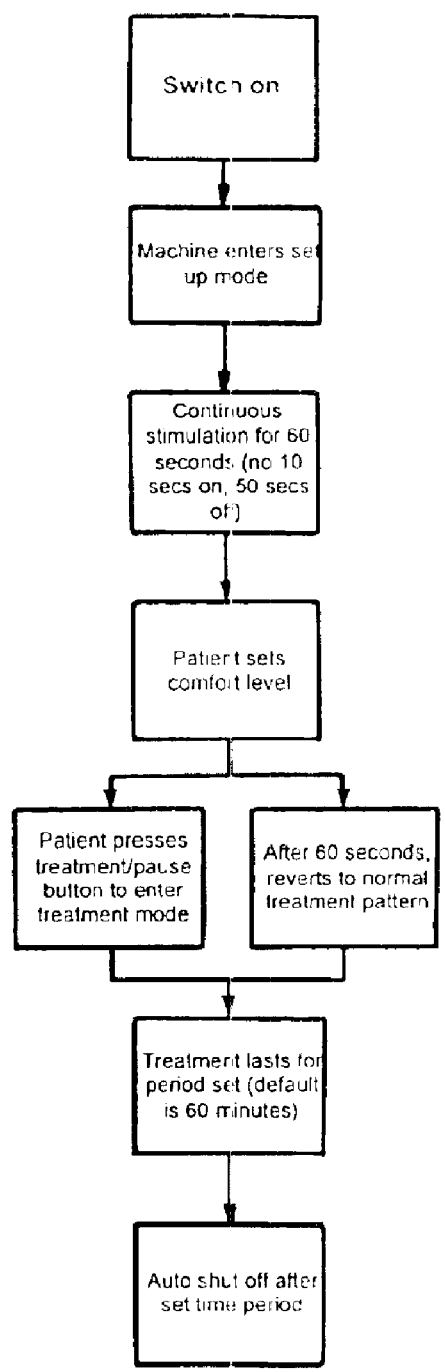
FIGS. 11 to 14 schematically represent logical processes followed in the use of the device shown in FIG. 10

FIG. 11 illustrates the set up phase of a treatment session. After initial switch-on, the machine enters a set up mode which generates a continuous stimulation for 60 seconds. Thus in this set up period a pulse pattern as illustrated in FIG. 4 is maintained for a continuous period of 60 seconds rather than the normal treatment mode of alternate stimulation and rest periods of 10 seconds and 50 seconds respectively. During this period the patient can set the amplitude of the applied pulses to a level which is comfortable by pressing the appropriate buttons 38 or 39. As soon as the patient is happy with the selected amplitude level, the treatment/pause button 41 is pressed to enter the treatment mode; whereafter, the pattern illustrated in FIGS. 2–4 is applied to that channel of the device. If the patient does not respond to the set up mode within 60 seconds the device automatically switches to the normal treatment pattern even if the treatment/pause button is not pressed.

The treatment then lasts for a period which may be set by the patient as described below. In default of the patient setting a treatment period, the treatment period lasts for 60 minutes. The system automatically shuts down after the set time period of 60 minutes if no period has been set by the patient.

Figure 12:
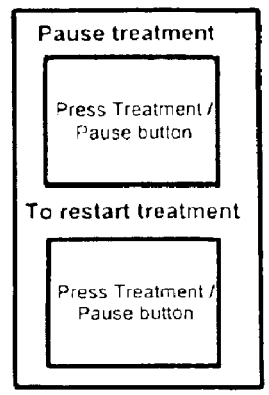

Referring to FIG. 12, at any time the patient can pause a previously programmed treatment simply by pressing the treatment/pause button. Similarly the patient can restart the treatment session by pressing the treatment/pause button again.

Figure 13:
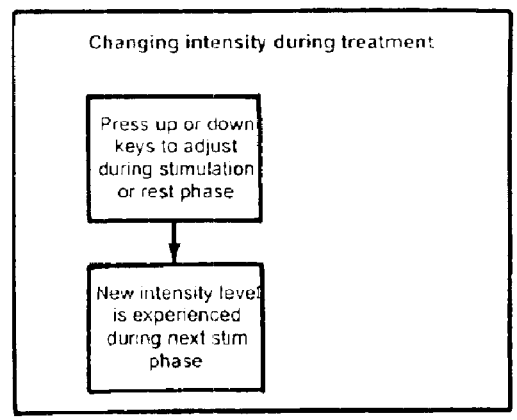

Referring to FIG. 13, the pulse amplitude is normally set to a level comfortable for the user during the set up mode. At any time during a treatment session however the pulse amplitude can be adjusted by the user applying pressure to the appropriate buttons 38 or 39. After such an adjustment the new pulse amplitude level is applied to the patient during the next 10 second duration stimulation phase. The system does not revert to the initially set amplitude level but maintains the adjusted level for the remainder of the treatment session.

Figure 14:
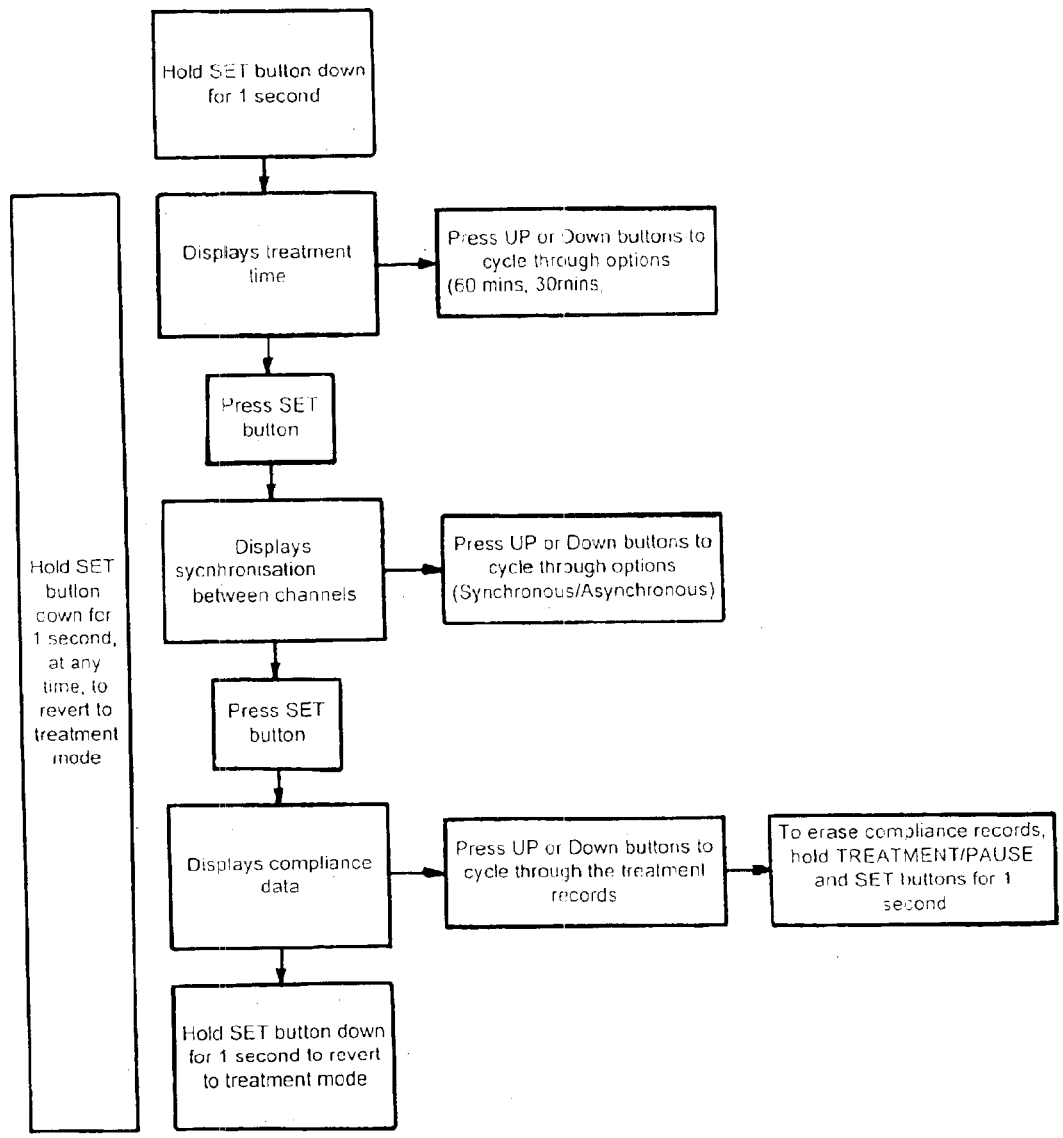

Referring to FIG. 14, initial treatment session set up is described in further detail. The patient initially holds down the set button 40 for 1 second. This then generates a display of a treatment time in the display areas 36 and 37 for the two channels. The buttons 38 and 39 respectively can then be pressed to cycle through pre-programmed options, for example 60 minutes, 30 minutes, continuous. Once the desired option has been selected the set button 40 is pressed again and thereafter a synchronisation mode between channels is displayed. Again the buttons 38, 39 can be pressed to cycle through options, that is synchronous/asynchronous. Once the appropriate option has been selected the set button 40 is pressed again and thereafter compliance data is displayed. The buttons 38 and 39 can be pressed to cycle through records of previous treatments applied via each of the channels. These records may be erased by holding the treatment/pause and set buttons 41, 40 down for 1 second. At any time, the device can be switched back to treatment mode simply by holding the set button 40 down for 1 second.

Figure 15:
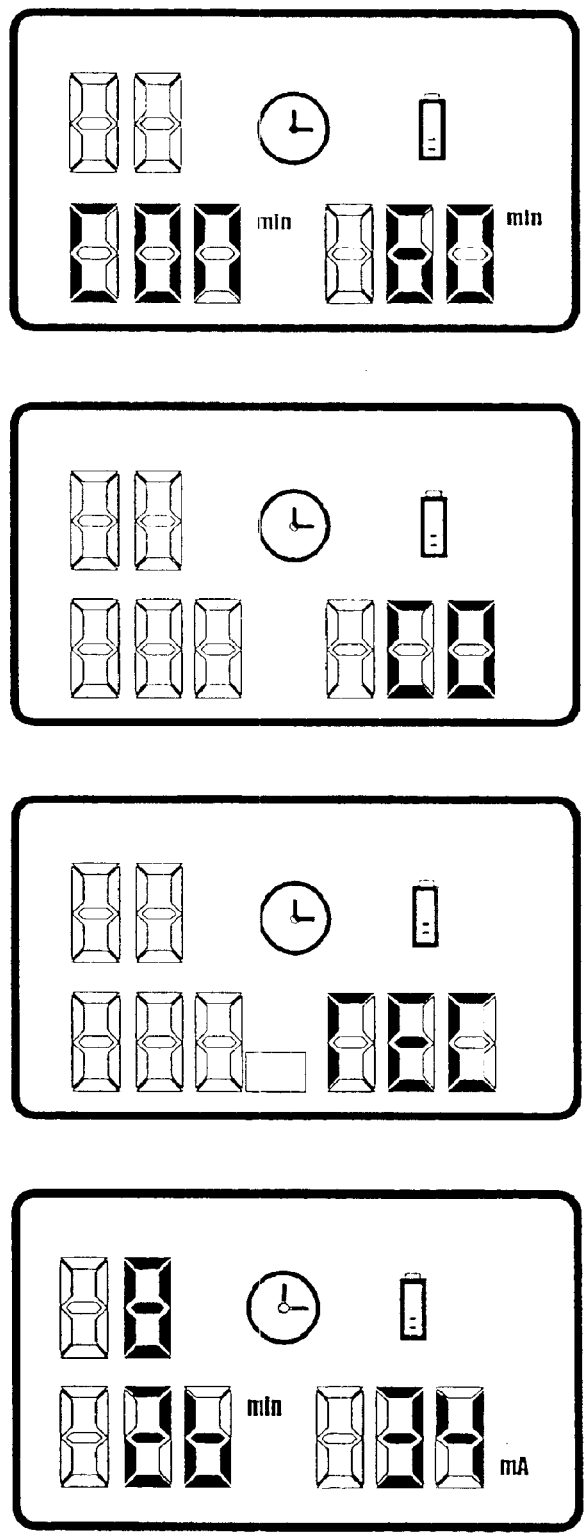
FIG. 15 shows output displays resulting from such use.

FIG. 15 shows for example displays which could be presented on the display area 32 of the handheld device 11. The uppermost display indicates a continuous treatment (con) on channel 1 and a 60 minutes treatment on channel 2. The second display indicates a synchronous treatment (referred to as co for co-contraction) as between channels 1 and 2. The third display indicates an asynchronous treatment (referred to as REC for reciprocal contraction) as between channels 1 and 2. The fourth display shows a possible compliance output with the display indicating that the eighth treatment was for 26 minutes at an average of 34 milliamps.

Thus, compliance data can be recorded and displayed on the handheld device itself. Preferably, however, the recorded compliance data will be downloaded to a PC via the cable 17 shown in FIG. 6. The same cable can be used by a clinician to adjust characteristics of the pulses applied to the patient which are not adjustable by the patient. For example, a clinician could enter into a PC connected to the cable 17 appropriate instructions to control the width of the pulses applied to the patient. Thus, although the patient would be in control of the pulse amplitude the pulse width would be under the control of the clinician. Generally the patient would be issued only with the handheld unit 11, the battery charger 13 and the electrodes 15. The handheld unit could be pre-programmed to switch to a preset pulse width of for example 100 microseconds which would be applied unless that default pulse width was adjusted by the clinician in the available range of from 50 microseconds to 350 microseconds.

Figure 16:
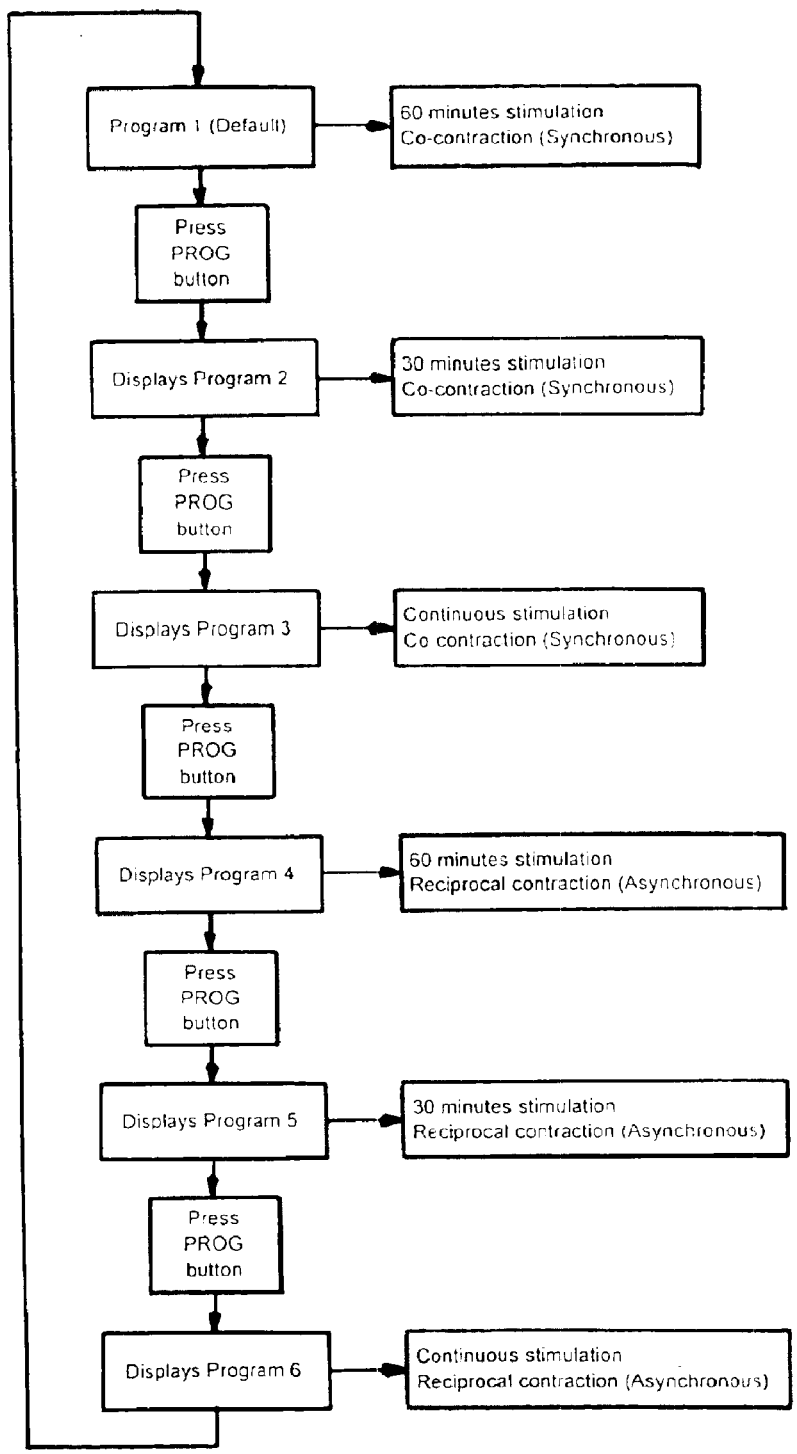
FIGS. 16 and 17 schematically represent alternative logical processes to those illustrated in FIGS. 11 to 14.
Figure 17:
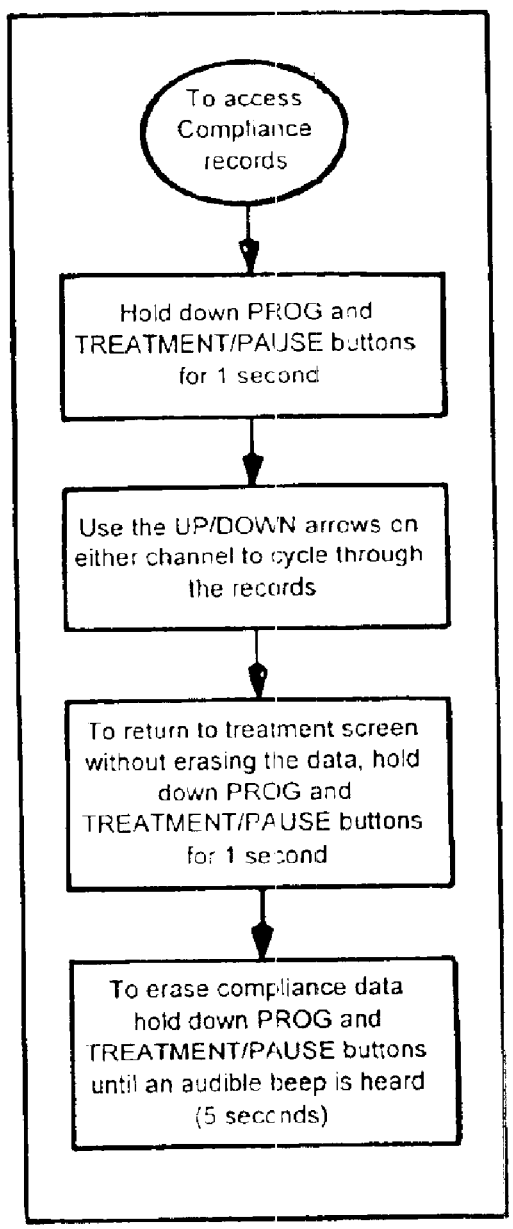

FIGS. 16 and 17 illustrate an alternative approach to enable a user to initiate a treatment session and to enable access to compliance data.

Referring to FIG. 16, on start-up the system will adopt a default condition which will deliver a 60 minutes co-contraction stimulation program. If the button 40 (see FIG. 10) is then pressed, this causes the system to step through a predetermined program, a single press causing the selection and display of a second program (30 minutes co-contraction, a further press causing the selection and display of a third program (continuous co-contraction), and so on as illustrated.

Referring to FIG. 17, when it is desired to access compliance data, the buttons 40 and 41 (FIG. 10) are pressed simultaneously for one second. The buttons 38 and 39 can be pressed to cycle through stored records data describing earlier use of each of the two channels. The user can return to the treatment mode of operation without deleting the stored records data by holding down buttons 40 and 41 for one second, and can return to the treatment mode of operation and delete the stored records data by holding down buttons 40 and 41 for five seconds, deletion of the records data being signalled by an audible output.

The most practical and preferred embodiment(s) of the invention described are described here. However, the invention is not to be limited to the disclosed embodiment(s). The invention includes other embodiments that incorporate the elements recited in the following claims and their equivalents.

What is claimed is:

1. An electrical muscle stimulator comprising:
   means for generating a predetermined stimulating signal, and
   means for applying the signal to a muscle,
   wherein the signal comprises a series of regularly spaced bursts of pulses, said bursts of pulses are separated by non-burst periods at least as long in duration as each of said bursts of pulses, wherein each of said bursts of pulses comprises a first component as a first continuous train of regularly spaced pulses and a second component as a series of regularly spaced second trains of regularly spaced pulses, the second component being combined with the first component and the spacing between successive pulses in the second trains being less than the spacing between successive pulses in the first continuous train.

2. A stimulator as claimed in claim 1, wherein each burst of pulses includes a third component as a series of regularly spaced third trains of regularly spaced pulses, the third component being combined with the first and second components, and the spacing between successive pulses in the third trains being less than the spacing between successive pulses in the second trains.

3. A stimulator as claimed in claim 2, wherein each burst of pulses consists of the same number of second and third trains.

4. A stimulator according to claim 3, wherein each third train immediately precedes one of said second trains.

5. A stimulator as claimed in claim 4, wherein each third trains consists of two pulses.

6. A stimulator as claimed in claim 3, wherein each third trains consists of two pulses.

7. A stimulator as claimed in claim 2, wherein each third trains consists of two pulses.

8. A stimulator as claimed in claim 2, wherein the first continuous train consists of pulses at 500 milliseconds intervals, each of the second trains consists of pulses at 20 milliseconds intervals, and each of the third trains consists of pulses of intervals of 12 milliseconds or less.

9. A stimulator as claimed in claim 8, wherein each of the second pulse trains consists of pulses timed at 0, 8, 20, 40, 60, 80, 100 and 500 milliseconds.

10. A stimulator as claimed in claim 8, wherein each of the second pulse trains consists of pulses timed at 0, 8, 28, 48, 68, 88, 108 and 500 milliseconds.

11. A stimulator as claimed in claim 1, further comprising means for enabling a user to adjust an amplitude of the pulses.

12. A electrical muscle stimulator comprising:
   means for generating a predetermined stimulating signal, and
   means for applying the signal to a muscle,
   wherein the signal comprises a series of regularly spaced bursts of pulses with each burst including a first component as a first continuous train of regularly spaced pulses and a second component as a series of regularly spaced second trains of regularly spaced pulses, the second component being combined with the first component and the spacing between successive pulses in the second pulse trains being less than the spacing between successive pulses in the first pulse train, and
   a battery powered hand-held unit with a single input/output connector, a battery charger, an electrode connector connected to said means for applying, and a computer connection cable, the battery charger, electrode connector and computer connection cable each being adapted to be connected to the single input/output connector such that the electrode connector cannot be connected to the hand-held unit if the hand-held unit is connected either to the battery charger or the computer connection cable.

13. A stimulator as claimed in claim 12, wherein the hand-held unit is programmable and is adaptable to be controlled by computer-generated signals applied to the single input/output connector to adjust the width of the pulses.

14. A stimulator as claimed in claim 12, wherein the hand-held unit further comprises means for storing patient treatment records data.

15. A stimulator as claimed in claim 14, further comprising means for outputting said patient treatment records data to the single input/output connector.

16. A method for electrically stimulating a muscle in which a stimulating signal is applied to the muscle, comprising:
   a) generating the stimulating signal, the signal comprising regularly spaced bursts of pulses and non-burst periods between said bursts, wherein said non-burst periods are each longer in duration than at least one of said bursts, wherein each of said bursts of pluses further comprises:
      (i) a first component as a first continuous train of regularly spaced pulses, and (ii) a second component as a series of regularly spaced second trains of regularly spaced pulses, wherein the second component is combined with the first component and the spacing between successive pulses in the second trains is less than the spacing between the successive pulses in the first continuous train, and b) applying the stimulating signal to the muscle.

17. A method as in claim 16 wherein each of the bursts of pulses further comprises a third component comprising a series of regularly spaced third trains of regularly spaced pulses, the third component being combined with the first and second components, and the spacing between successive pulses in the third trains being less than the spacing between successive pulses in the second pulse trains.

18. A method as in claim 17 wherein each burst of pulses consists of the same number of second and third trains.

19. A method as in claim 17 wherein each third pulse train immediately precedes a respective second pulse train.

20. A method as in claim 17 wherein each third train consists of two pulses.

21. A method as in claim 18 wherein each third train consists of two pulses.

22. A method as in claim 19 wherein each third train consists of two pulses.

23. A method as in claim 17 each second pulse train comprises of pulses timed at 0, 8, 28, 48, 68, 88, 108 and 500 milliseconds.

24. A method as in claim 16 wherein the first continuous train comprises pulses at 500 milliseconds intervals, each second pulse train comprises pulses at 20 milliseconds intervals, and each third train comprises pulses of intervals of 12 milliseconds or less.

25. A method as in claim 16 wherein each second pulse train comprises pulses timed at 0, 8, 20, 40, 60, 80, 100 and 500 milliseconds.

* * * * *